(12) United States Patent
Aryal

(10) Patent No.: US 9,205,034 B2
(45) Date of Patent: Dec. 8, 2015

(54) LOTION TABLET THAT PROVIDES OXYGEN

(71) Applicant: AVENT, INC., Alpharetta, GA (US)

(72) Inventor: Shruti Aryal, Beaverton, OR (US)

(73) Assignee: Avent, Inc., Alpharetta, GA (US)

( * ) Notice: Subject to any disclaimer, the term of this patent is extended or adjusted under 35 U.S.C. 154(b) by 12 days.

(21) Appl. No.: 13/692,203

(22) Filed: Dec. 3, 2012

(65) Prior Publication Data

US 2014/0154318 A1    Jun. 5, 2014

(51) Int. Cl.
| | |
|---|---|
| *A61K 8/22* | (2006.01) |
| *A61Q 19/00* | (2006.01) |
| *A61Q 19/08* | (2006.01) |
| *A61Q 19/10* | (2006.01) |
| *A61K 8/11* | (2006.01) |
| *A61K 8/19* | (2006.01) |
| *A61Q 19/02* | (2006.01) |

(52) U.S. Cl.
CPC ... *A61K 8/22* (2013.01); *A61K 8/11* (2013.01); *A61K 8/19* (2013.01); *A61Q 19/00* (2013.01); *A61Q 19/08* (2013.01); *A61Q 19/10* (2013.01); *A61Q 19/02* (2013.01)

(58) Field of Classification Search
CPC ....... A61Q 19/08; A61Q 19/10; A61Q 19/00; A61Q 19/02; A61K 8/19; A61K 8/22; A61K 8/11
See application file for complete search history.

(56) References Cited

U.S. PATENT DOCUMENTS

| | | | |
|---|---|---|---|
| 2,245,495 A | * | 6/1941 | Pemble .................... 252/186.24 |
| 4,155,868 A | | 5/1979 | Kaplan et al. |
| 4,867,988 A | * | 9/1989 | Chernack ...................... 424/490 |
| 5,736,582 A | | 4/1998 | Devillez |
| 2002/0147123 A1 | * | 10/2002 | Becker et al. ................. 510/305 |
| 2006/0121101 A1 | | 6/2006 | Ladizinsky |
| 2008/0145437 A1 | * | 6/2008 | Amundson et al. ........... 424/490 |
| 2009/0054295 A1 | * | 2/2009 | Vicari et al. .................. 510/380 |
| 2009/0252815 A1 | | 10/2009 | Walzer et al. |

FOREIGN PATENT DOCUMENTS

WO    WO 98/53836 A1    12/1998

\* cited by examiner

*Primary Examiner* — Anoop Singh
*Assistant Examiner* — Doan Phan
(74) *Attorney, Agent, or Firm* — Dority & Manning, P.A.

(57) ABSTRACT

There is provided a lotion tablet for the delivery of oxygen having an outer layer or "crust" coating an interior, that liberates oxygen upon rupture of the crust. The oxygen may be generated in the interior upon rupture of the crust or may be pre-formed or dissolved in the interior prior to coating the interior with the crust. The tablet would be easy to carry in airplanes, for example, making it readily available to the customer. Furthermore, the consumer may peel/tear open as many tablets as they desire, according to their needs/preference.

9 Claims, No Drawings

LOTION TABLET THAT PROVIDES OXYGEN

The present disclosure relates to the provision of oxygen for use in cosmetic formulations.

The lack of oxygen, i.e. hypoxia, is commonly experienced by people in their extremities as they get older due to poor blood circulation as well as by those with conditions such as diabetes. Studies have also shown below normal, low oxygen tension in the skins of older people. This often leads to poor skin health and an excessive presence of visible conditions such as wrinkles, dryness and lower skin elasticity. Over the years, cosmetic manufacturers have introduced skin formulations with a large variety of ingredients such as emollients, exfoliators, moisturizers etc., to retard these age related effects and improve and maintain skin health. Attacking the problem of low oxygen directly has not been generally practiced.

The delivery of oxygen to the skin for common use is a technological challenge, since oxygen is quite reactive and unstable. High concentrations of oxygen could not be provided for home use because of this instability. Oxygen can, however, be provided in the form of a peroxide and a peroxide decomposition catalyst per US patent publication 2006/0121101 to Ladizinsky. This publication provides such a treatment for intact skin through the use of a dressing that is applied to an area of the skin. The dressing generally has a rupturable reservoir containing an aqueous hydrogen peroxide composition and a hydrogel layer having a peroxide decomposition catalyst. Unfortunately the catalytic decomposition of hydrogen peroxide to oxygen is quite rapid and so the dressing has a layer that is impermeable to oxygen on the outside so that the oxygen is held against the skin for the maximum time possible. While this dressing is useful for small areas of the skin, it should be clear that it is unworkable for large areas or irregularly shaped areas of skin.

Alternatively, Devillez (U.S. Pat. No. 5,736,582) proposes the use of hydrogen peroxide in the place of benzoyl peroxide in skin treatment compositions that also contain solvents for hydrogen peroxide. This allows the hydrogen peroxide to stay below a level that will damage the skin and to stay in solution in greater concentrations. A solvent such as dimethyl isosorbide along with water is taught as being effective. No peroxide decomposition catalyst is present. Unfortunately, no data on oxygen concentration or generation are given, nor is the time required for oxygen liberation. While this method appears to be an advance over non-oxygen containing compositions, the lack of data makes it difficult to make objective judgments on the overall effectiveness of this approach. Given the concentrations of peroxide, however, it is doubtful that significant volumes of oxygen were generated.

There is a need for an easy-to-use way of applying oxygen to the skin. Such a method and/or product should have relatively few components and be intuitive to use, without the need for special dressings or other awkward requirements. A product that may be used in a manner similar to known products would be most readily accepted by the consumer.

SUMMARY

The problem discussed above has found a solution to a large degree in the present disclosure, which describes the use of a tablet that may contain or generate oxygen. The oxygen is released or "liberated" when the tablet is used.

There is provided a lotion tablet for the delivery of oxygen. The tablet has an outer layer or "crust" coating an interior, that liberates oxygen upon rupture of the crust. The oxygen may be generated in the interior upon rupture of the crust or may be pre-formed or dissolved in the interior prior to coating the interior with the crust.

The tablet would be easy to carry in airplanes, for example, making it readily available to the customer. Furthermore, the consumer may peel/tear open as many tablets as they desire, according to their needs/preference.

To impart additional cosmetically desirable properties, the component compositions may contain other ingredients such as natural or synthetic polymers, moisturizers, humectants, viscosity modifiers, emollients, texture enhancers, UV blocking agents, colorants, pigments, ceramics (fumed silica, titanium dioxide, natural and synthetic clays), antioxidants, fragrances etc.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The application of oxygen to the skin can help to alleviate a number of problems brought on by ageing such as poor skin health and an excessive presence of visible conditions such as wrinkles, dryness and lower skin elasticity. Oxygen applied to the skin can help to retard these age related effects and improve and maintain skin health.

Applying oxygen to the skin topically through the application of a liquid or foam composition is a convenient, easy and quick method of delivering the desired benefits discussed above. A two part formulation helps to ensure that the oxygen is available for use and has not been lost during storage, but can present a challenge for product developers because of the need to keep the two ingredients separate and combine them at the proper time.

The disclosed tablet as an individualized aliquot of lotion offers many useful features compared to conventional liquid lotion from a pump or squeeze bottle. The solid lotion tablet is easy to use and it's portable. An aging hand, for example, might find it very difficult to squeeze or pump a bottle especially when the amount of lotion remaining in the container is low. Compared to this situation, tearing and/or peeling actions are much simpler. The tablet would also be easy to carry in airplanes, making it readily available to the customer. Furthermore, the consumer may peel/tear open as many tablets as they desire, according to their needs/preference.

The lotion tablet described herein has regular lotion ingredients such as oils and waxes, water and fragrances, but is in a solid or semi-solid form with an outer layer. Each tablet may be packaged individually in a form that would be easy to peel or tear open at the time of use. The aliquot of lotion in each tablet may be sized to sufficiently hydrate and moisturize skin and readily dissolve and be absorbed upon direct contact to the skin and to be acceptable for airline or other size restrictions.

The lotion tablet disclosed herein generally has three layers, though in some embodiments the middle layer is optional. For ease of understanding and reference, the layers will be referred to in a manner analogous to the layers of the Earth; core, mantle and crust. The core is the innermost layer, covered by the mantle, which is in turn covered by the outer layer or "crust". The core and mantle collectively comprise the interior of the lotion tablet. These terms are merely descriptive of their relative positions however, and do not refer to any particular physical properties. Note also that the lotion tablet need not be round but may be in any usable shape.

The "crust" of the tablet may be an outer layer, covering or coating of a wax, oil or solid that functions to seal in the lotion containing the oxygen generating chemistries and/or the oxygen. The crust completely covers the mantle, which desirably completely covers the core. When the crust of the tablet is ruptured, the oxygen is liberated. The crust is desirably a bee's wax having a melting point between about 20 and 60 deg. C. Alternatively the crust material may be a paraffin wax, an organic polymer like polyethylene glycol (PEG), polypropylene glycol (PPG), polyvinyl pyrrolide (PVP), methyl cellulose or derivatives thereof like carboxy methyl cellulose and hydroxy propyl methyl cellulose. The crust may be applied to the mantle by dipping the mantle into the crust, by spraying and other known suitable methods.

The interior of the tablet is in a semi-solid form and contains lotion and other ingredients that can be utilized to quickly generate oxygen "on demand", i.e., at the time of usage when the crust is ruptured. Alternatively, the tablet can contain pre-formed oxygen bubbles/and or dissolved oxygen using such ingredients, that are released when the crust is ruptured.

The liberation of oxygen that is generated "on-demand" may be accomplished by utilizing entrapped chemistries. Examples of such ingredients or chemistries include a catalyst and hydrogen peroxide in a way that no (or virtually no) residue of the ingredients is left behind or absorbed into the skin. Prior to use, the chemistries would be either be depleted in the reaction or be neutralized by some mechanism of action (discussed below). The interior of the tablet may be made with two layers; core and mantle, one having the hydrogen peroxide and the other having the catalyst. For example, the core could contain a dilute solution of hydrogen peroxide at a relatively high viscosity and this core could be enveloped by a mantle containing the catalyst. The core may be made by cooling the core ingredients, coating the core with the mantle to create the interior and again cooling, and then applying the crust. The positions of the catalyst and peroxide may be reversed, with the core having the catalyst and the mantle having the peroxide.

The liberation of oxygen that is trapped and pre-formed in the form of oxygen bubbles or in the form of dissolved oxygen in the lotion may be accomplished without using the "on demand" oxygen generating system described above. In this embodiment, ingredients that generate oxygen are brought together, oxygen is generated, but the oxygen is trapped within the crust of the tablet. A dilute hydrogen peroxide solution may be mixed with a catalyst to produce a relatively high viscosity mixture, and, as oxygen is generated, the mixture is cooled to trap the oxygen in the mixture. The mixture may be optionally coated with a mantle of moisture rich hydrogel if desired prior to coating with the crust, in order to improve the feel of the tablet ingredients on the skin and deliver other benefits.

The catalyst in any of the embodiments may be catalase, manganese dioxide ($MnO_2$) or a base such as sodium carbonate ($Na_2CO_3$). The catalyst catalyzes the reaction from hydrogen peroxide to oxygen and water. Manganese dioxide may not be favored for this application, however, since it may leave a dark residue. Manganese dioxide may be used if the user is less concerned about the treated area being seen. For example, if the human skin to which the oxygen is to be applied is in a less visible area or if it is desired to apply the oxygen to a non-human animal, a dark residue may not be of concern.

EXAMPLE 1

Pre-Formed Oxygen Bubbles/and or Dissolved Oxygen

Step 1: Preparation of Oxygen Rich Oil Emulsion Core.

Hydrogen peroxide in an emulsion was made from an original concentration of 35% w/w hydrogen peroxide solution (Spectrum HY115; New Brunswick, N.J.) added to a commercially available lotion base (Evonik Industries, product 1564-06) to produce a final concentration of 0.9% w/w hydrogen peroxide.

Alternatively, a water in oil emulsion may be made to which the hydrogen peroxide solution may be added to reach a final concentration of 0.9%-1% hydrogen peroxide in the emulsion. To prepare a water in oil emulsion, a first aqueous mixture consisting of water with water soluble thickeners and surfactants is made. An oil phase consisting of different types of oils and oil soluble surfactants/emulsifiers is also prepared. The water with thickeners and surfactants is slowly added to the oil phase containing the emulsifiers with stirring. 35% hydrogen peroxide may be pre-diluted or added straight to the emulsion depending on the volume of liquid desired to reach a desired viscosity of the emulsion, desirably >100,000 cps.

In an alternative embodiment, an aqueous phase mixture was prepared with 4% hydroxy ethyl cellulose (HEC) by mixing 12 g HEC to 300 g of de-ionized water. After mixing the slurry, the mixture was heated to 80 deg C. to activate the HEC so that it thickened. Then the suspension was cooled to room temperature. Alternatively, other thickeners such as carboxymethyl cellulose or Carbomers, guar gum, xanthan gum or combination of one or the others may also be used. Some thickeners may make slightly acidic suspensions and may need to be neutralized by addition of a base. The final pH of the thickener should be checked and be made neutral or close to neutral (5.5-7).

The oil phase was prepared using silicone oil with jojoba oil and lecithin (emulsifier) up to 1.5% purchased from "making cosmetics" website. In one particular instance, Aerosil 816R silica (hydrophobic nano-silica particle from Evonik) was also added for up to 2% by weight in the final oil mixture. This nano-silica was added to enhance the stabilization of the emulsion and preserve the oxygen content of this phase, which will be the very inner core of the tablet. Other cosmetic oils, Perfluorodecalin oil or fragrances may also be used as long as the densities of the fluids are consistent and are miscible with one another.

For the preparation of water in oil emulsions, the oil phase components were added first in the following order with homogenization after adding the emulsifiers. First, oils were mixed, then lecithin is added and homogenized, then aerosol silica is added and the mixture homogenized. Finally, the water phase (prepared earlier ~4% HEC or other thickeners) is slowly added as the emulsion is mixed in high shear with a homogenizer (~10,000 rpm). The final concentration of the emulsion was 50%-55% oils and emulsifiers with the remainder of aqueous phase mix. The resulting emulsion was a thick viscoelastic fluid which rubbed into the skin upon application. To this, the 35% hydrogen peroxide solution was added to have 1% hydrogen peroxide in the final emulsion stock.

The oxygen reservoir basic (pH greater than 7) solution of sodium carbonate ($Na_2CO_3$ from Armesco) was also prepared separately in de-ionized water. A 20% $Na_2CO_3$ stock solution of this basic water was prepared and may be stored for at most a week at room temperature. A fresh solution is desired and so more than 1 week old solution was thrown away and prepared fresh as needed.

50 g of the hydrogen peroxide emulsion stock was weighed into a plastic container to which 10 ml of 20% Na2CO3 solution was added and mixed well to react so that oxygen bubbles were formed inside the semi-solid matrix. It is desired to have a final pH of between 8 and 10, more desirably about 9. Ideally, the mixture is mixed thoroughly (e.g. with a vortex), then centrifuged for (~2 min) at 5000 rpm to remove any bubbles. However, this is not always possible because centrifuges can only take certain sizes of tubes and for a larger samples in beakers, the centrifugation step may be eliminated.

When the mixture was ready, it was transferred to an ice tray, and then placed in 40 deg C. oven to let the base react with peroxide to generate oxygen. This should be checked periodically (approximately every 30 min) to see if bubbles are forming. The presence of bubbles indicates that oxygen is forming and the reaction is proceeding normally. Once it was visible that lots of bubbles were forming, the tray was immediately removed, covered entirely with PARAFILM and a tooth pick was placed perpendicularly in the center of each of the emulsion portions through the PARAFILM. The tray was frozen at minus 80 deg C. for at least 1 hour.

PARAFILM is a commercially available film that stretches greatly and clings to irregular shapes, from Sigma Aldrich. It is advisable to not put the PARAFILM cover in place prior to incubation in the oven as the heat may cause the PARAFILM to soften or melt on to the plastic tray, which then makes it difficult to remove.

As an alternate solution to the base used here, a catalase solution may also be used as a catalyst to generate oxygen. Typically, catalase solution would have to be diluted in buffer and a certain amount added to the emulsion or to a skin hydrator like those commercially available from Evonik Industries as product 1553-11. This reaction proceeds very quickly and lots of oxygen bubbles are generated. Once the catalase is added and mixed well, the emulsion is quickly dispensed into an ice tray as described above, PARAFILM is placed on top followed by a tooth pick in the center of each cubicle of the tray. This need not be heated as reaction of the peroxide with catalase is very quick and doesn't require heat. Once the bubbles start to form, the tray is then frozen at minus 80 deg C. for an hour or until frozen.

Step 2 (Optional): Coating with a Moisture Rich Hydrogel.

The frozen oxygen rich emulsion of step 1 may be coated with a hydrogel to help neutralize any residual base used in the core. It is an optional layer that may be deleted if desired.

In this example, the frozen, oxygen rich emulsion of step 1 was dipped into a moisture rich hydrogel to encapsulate the emulsion. The moisture rich hydrogel used in this example was mixture of glycerin (20%-30%), HEC, Polysorbate 60 (emulsifier), and water. Use of oils in this hydrogel layer is optional (up to 4%) due to the presence of emulsifiers such as Polysorbate 60 which makes the aqueous phase more miscible to oils. Different ratios of the above water soluble compounds may be used or a different type of a thickener may also be used.

It is also optional to make this layer acidic (1-2 pH). There are two functional aspects to the acidity of this layer; acid will neutralize any residual base ($Na_2CO_3$) used in the core phase (above) when the tablet is rubbed and melted into the skin. Secondly, the acidity will also decrease the solubility of oxygen in this layer making it less likely for the entrapped oxygen of the core (oil rich emulsion) to escape.

For coating the tablet with this layer, remove the frozen, oxygen rich emulsions from the refrigerator. Thaw in the refrigerator at 20 deg C. for 1 to 2 hours if they are too hard to handle (or until the tray is movable). Remove the PARAFILM from the top, carefully keeping the toothpicks intact in each of the tablet cores. Gently remove one frozen tablet at a time and quickly dip it into the hydrogel and remove. Quickly place the dipped tablets back into the original position in the tray. Repeat for all tablets. Cover with PARAFILM once again. Then freeze in a freezer at minus 80 deg C. for at least an hour or until frozen completely.

Step 3: Crust.

The frozen, hydrogel coated, oxygen rich, water in oil emulsion was coated with wax to help keep the tablet in solid form at room temperature. The wax used was commercially available, cosmetic grade bees' wax.

A typical wax coating was prepared from a melted blend of low melting bees' wax (≤¼ oz.), Shea butter, cocoa butter, mineral oil, jojoba oil and oil phase emulsifier such as lecithin. This blend has not been optimized and so many different proportions or amount of one or more oils, butters and bees' waxes may be tried. It is important to have at least one type of emulsifier, such as lecithin, in an amount up to 2% by weight total.

The method of preparation is a double broiler method. A steel pan containing some water is heated on top of a heat plate. An empty glass beaker is place on top of the pan. Bees wax is slowly added to the empty glass beaker and melted by increasing the temperature to >60 deg C. or a temperature slightly greater than the melting temperature of the wax. In a separate container, all butters (solid at room temperature) are weighed into a cup and melted in a microwave oven. Once the wax is thoroughly melted, the oils are gently added into the wax. Some may start to solidify but they will eventually be melted as long as the melting temperature of all oils and waxes is maintained. Lecithin is added at the end and mixed well.

EXAMPLE 2

On-Demand Generation of Oxygen. Core of Hydrogen Peroxide

Step 1: Preparation of Hydrogen Peroxide Core.

The hydrogen peroxide core would be prepared as described in step 1 of Example 1, except that neither Na2CO3 nor catalase would be added to the solution. The solution would be cooled as described above.

Step 2: Coating the Core with a Catalyst Mantle.

A hydrogel may be used in this example. The hydrogel may be a mixture of glycerin (20%-30%), HEC, Polysorbate 60 (emulsifier), and water. To this hydrogel may be added the catalyst, and the mixture coated onto the innermost core with cooling as described above.

For catalase: a catalase solution (from Bio-Cat Inc.), would be diluted in a phosphate buffer solution such that the final concentration of the catalase in the hydrogel would be 1000-1300 U. This should not be acidic as this would de-stabilize the catalase. The viscosity should be around ~100,000 cps. One needs to be able to dip the frozen core properly and an overly thick solution would make this difficult. If a different method than dipping is used, however, the viscosity may be higher. The core would be coated and cooled as described in step 2 of Example 1.

Step 3: Crust.

The frozen tablet from step 2 would be coated with wax to help keep the tablet in solid form at room temperature as described in step 3 of Example 1.

EXAMPLE 3

On-Demand Generation of Oxygen. Core of Catalyst

Step 1: Preparation of Catalyst Core.

An water in oil emulsion may be made to which the catalyst solution may be added. To prepare a water in oil emulsion, a first aqueous mixture consisting of water with water soluble thickeners and surfactants is made. An oil phase consisting of different types of oils and oil soluble surfactants/emulsifiers is also prepared. The water with thickeners and surfactants is slowly added to the oil phase containing the emulsifiers with stirring. The catalyst may be pre-diluted or added straight to the emulsion depending on the volume of liquid desired to reach a desired viscosity of the emulsion, desirably >100,000 cps.

Step 2: Coating the Core with a Peroxide Mantle.

A hydrogel would be prepared as described in step 2 of Example 2. A dilute (1%) solution of hydrogen peroxide would be added to the hydrogel. The solution would be coated onto the cooled core and again cooled, as described in step 2 of Example 1.

Step 3: Crust.

The frozen tablet from step 2 would be coated with wax to help keep the tablet in solid form at room temperature, as described in step 3 of Example 1.

While the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. A lotion tablet for the delivery of oxygen to skin comprising a rupturable crust covering an interior having a core and a mantle, wherein the mantle covers the core, wherein one of said core and mantle is a peroxide and other is a catalyst that catalyzes the conversion of peroxide to oxygen and water, wherein the oxygen is liberated and delivered to the skin in an aliquot of lotion upon rupture of the crust as the tablet is rubbed into the skin.

2. The lotion tablet of claim 1 wherein said oxygen is generated by said interior upon rupture of the crust.

3. The lotion tablet of claim 1 wherein said peroxide comprises hydrogen peroxide.

4. The lotion tablet of claim 3 wherein said peroxide is present at a concentration of about 1 weight percent in a water in oil emulsion.

5. The lotion tablet of claim 1 wherein said catalyst is selected from the group consisting of catalase, manganese dioxide and sodium carbonate.

6. The lotion tablet of claim 1 wherein said crust comprises a wax or oil.

7. A lotion tablet for delivery of oxygen to skin comprising a rupturable crust covering an interior having a core, wherein said core comprises an oxygen rich emulsion formed from a mixture of hydrogen peroxide and a catalyst that catalyzes the conversion of hydrogen peroxide to oxygen and water, wherein the oxygen is liberated and delivered to the skin in an aliquot of lotion upon rupture of the crust as the tablet is rubbed into the skin.

8. The lotion tablet of claim 7 wherein said catalyst is selected from the group consisting of catalase, manganese dioxide and sodium carbonate.

9. The lotion tablet of claim 7 further comprising a moisture rich hydrogel mantle between the core and the crust.

\* \* \* \* \*